(12) United States Patent
Aw et al.

(10) Patent No.: US 11,964,100 B2
(45) Date of Patent: *Apr. 23, 2024

(54) HEATER ASSEMBLY WITH CAVITY FILLED WITH A POTTING COMPOUND

(71) Applicant: Philip Morris Products S.A., Neuchatel (CH)

(72) Inventors: Sze Chiek Aw, Singapore (SG); Jean Luc Fringeli, Singapore (SG); Chow Kian Yeo, Singapore (SG)

(73) Assignee: Philip Morris Products S.A., Neuchatel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/858,522

(22) Filed: Jul. 6, 2022

(65) Prior Publication Data

US 2022/0339374 A1 Oct. 27, 2022

Related U.S. Application Data

(62) Division of application No. 16/620,588, filed as application No. PCT/EP2018/070519 on Jul. 27, 2018, now Pat. No. 11,413,411.

(30) Foreign Application Priority Data

Jul. 28, 2017 (EP) ..................................... 17183836

(51) Int. Cl.
*A61M 15/06* (2006.01)
*A24F 40/46* (2020.01)
(Continued)

(52) U.S. Cl.
CPC ............. *A61M 15/06* (2013.01); *A24F 40/46* (2020.01); *A24F 40/70* (2020.01);
(Continued)

(58) Field of Classification Search
CPC .......... A24F 40/20; A24F 40/46; A24F 40/70; A61M 15/06; H05B 3/44
See application file for complete search history.

(56) References Cited

U.S. PATENT DOCUMENTS

| 9,674,894 B2 | 6/2017 | Schneider |
| 11,413,411 B2* | 8/2022 | Aw ........................... H05B 3/44 |

(Continued)

FOREIGN PATENT DOCUMENTS

| CN | 103974640 A | 8/2014 |
| CN | 104470387 A | 3/2015 |

(Continued)

OTHER PUBLICATIONS

U.S. Appl. No. 16/620,588, filed Dec. 9, 2019, 2020/0178605 A1, Sze Chiek AW, et al.
(Continued)

*Primary Examiner* — Hae Moon Hyeon
(74) *Attorney, Agent, or Firm* — Oblon, McClelland, Maier & Neustadt, L.L.P.

(57) ABSTRACT

A heater assembly for an aerosol-generating device is provided, the heater assembly including: a bushing defining an aperture at a first end of the bushing and a cavity at a second end of the bushing; and an elongate electrical heater extending from the first end of the bushing, in which a portion of the elongate electrical heater extends through the aperture and into the cavity. An aerosol-generating device, and an aerosol-generating system, are also provided.

16 Claims, 4 Drawing Sheets

(51) Int. Cl.
  *A24F 40/70* (2020.01)
  *B29C 45/14* (2006.01)
  *H05B 3/03* (2006.01)
  *H05B 3/44* (2006.01)
  *A24F 40/20* (2020.01)
  *B29L 31/00* (2006.01)
  *B29L 31/18* (2006.01)

(52) U.S. Cl.
  CPC ......... *B29C 45/14336* (2013.01); *H05B 3/03* (2013.01); *H05B 3/44* (2013.01); *A24F 40/20* (2020.01); *B29C 2045/14459* (2013.01); *B29L 2031/18* (2013.01); *B29L 2031/7414* (2013.01)

(56) References Cited

U.S. PATENT DOCUMENTS

| | | | | |
|---|---|---|---|---|
| 2014/0261408 | A1* | 9/2014 | DePiano | A24F 40/46 128/202.21 |
| 2015/0163859 | A1 | 6/2015 | Schneider | |
| 2016/0066621 | A1 | 3/2016 | DePiano et al. | |
| 2017/0095002 | A1 | 4/2017 | Silvestrini | |
| 2018/0049471 | A1 | 2/2018 | Holoubek et al. | |
| 2018/0235278 | A1 | 8/2018 | Mahler | |
| 2018/0303168 | A1 | 10/2018 | DePiano et al. | |

FOREIGN PATENT DOCUMENTS

| | | |
|---|---|---|
| CN | 105212277 A | 1/2016 |
| CN | 105595422 A | 5/2016 |
| CN | 205197003 U | 5/2016 |
| CN | 106376975 A | 2/2017 |
| CN | 106793833 A | 5/2017 |
| JP | 2015-508287 A | 3/2015 |
| JP | 2017-69084 A | 4/2017 |
| JP | 2017-518761 A | 7/2017 |
| KR | 10-2015-0060964 A | 6/2015 |
| KR | 10-2015-0099704 | 9/2015 |
| KR | 10-2015-0130460 | 11/2015 |
| KR | 10-2016-0145838 A | 12/2016 |
| WO | 2010/107613 A1 | 9/2010 |
| WO | WO 2015/155289 A1 | 10/2015 |
| WO | 2015/197627 A1 | 12/2015 |
| WO | 2016/124552 A1 | 8/2016 |

OTHER PUBLICATIONS

Korean Notice of Allowance dated Mar. 24, 2023 in Korean Application 10-2019-7037782, (with English translation), 4 pages.
Japanese Office Action dated Sep. 12, 2022 in Japanese Patent Application No. 2019-570484 (with English translation), 7 pages.
Combined Chinese Office Action and Search Report dated Oct. 19, 2022 in Chinese Patent Application No. 201880040843.0 (with English translation), 12 pages.
International Search Report and Written Opinion dated Dec. 11, 2018 in PCT/EP2018/070519 filed on Jul. 27, 2018.
"LOCTITE® SI 5091™ Known as LOCTITE® 5091" LOCTITE® Technical Data Sheet, Apr. 2017, 3 pages.
Russian Notice of Allowance and Search Report dated Jan. 24, 2022 in corresponding Russian Patent Application No. 2019142109, 18 pages.
Korean Office Action dated Dec. 13, 2022 in Korean Patent Application No. 10-2019-7037782 (with English Translation), 8 pages.
Korean Office Action mailed on Feb. 1, 2024 issued on Korean Patent Application No. 10-2023-7020972 filed on Jul. 27, 2018, with English Translation, total 11 pages.

* cited by examiner

HEATER ASSEMBLY WITH CAVITY FILLED WITH A POTTING COMPOUND

CROSS-REFERENCE TO RELATED APPLICATIONS

This application is a divisional of and claims benefit under 35 U.S.C. § 120 to U.S. application Ser. No. 16/620,588, filed on Dec. 9, 2019, which is a U.S. national stage application of PCT/EP2018/070519, filed on Jul. 27, 2018, which is based upon and claims the benefit of priority under 35 U.S.C. § 119 to European Application No. 17183836.0, filed Jul. 28, 2017, the entire contents of each of which are incorporated herein by reference.

TECHNICAL FIELD

The present invention relates to a heater assembly for an aerosol-generating device, the heater assembly having a cavity. The present invention also relates to an aerosol-generating device comprising the heater assembly, an aerosol-generating system comprising the aerosol-generating device, a method of generating an aerosol, and a method of assembling a heater assembly.

DESCRIPTION OF THE RELATED ART

One type of aerosol-generating system is an electrically operated smoking system. Known handheld electrically operated smoking systems typically comprise an aerosol-generating device comprising a battery, control electronics and an electric heater for heating a smoking article designed specifically for use with the aerosol-generating device. In some examples, the smoking article comprises a plug of an aerosol-forming substrate, such as a tobacco plug, and the heater contained within the aerosol-generating device is inserted into the aerosol-forming substrate when the smoking article is inserted into the aerosol-generating device.

Aerosol-generating articles for electrically operated smoking systems typically exhibit a high liquid content to facilitate generation of an aerosol when heated. During use, liquid from the aerosol-generating article may collect within the aerosol-generating device, either through direct transfer from the aerosol-generating article, or as a result of the condensation of aerosol within the aerosol-generating device. The liquid that collects within the aerosol-generating device during use may leak into the interior of the aerosol-generating device and result in the deterioration or failure of electrical components within the aerosol-generating device.

It would be desirable to provide a heater assembly for an aerosol-generating device that reduces or eliminates the potential for the leakage of liquid into the aerosol-generating device during use.

SUMMARY

According to a first aspect of the present invention there is provided a heater assembly for an aerosol-generating device, the heater assembly comprising a bushing defining an aperture at a first end of the bushing and a cavity at a second end of the bushing. The heater assembly also comprises an elongate electrical heater extending from the first end of the bushing, wherein a portion of the elongate electrical heater extends through the aperture and into the cavity.

According to a second aspect of the present invention there is provided an aerosol-generating device comprising a heater assembly according to the first aspect of the present invention, in accordance with any of the embodiments described herein.

According to a third aspect of the present invention there is provided an aerosol-generating system comprising an aerosol-generating device according to the second aspect of the present invention, in accordance with any of the embodiments described herein.

According to a fourth aspect of the present invention, there is provided a method of generating an aerosol. The method comprises providing an aerosol-generating device according to the second aspect of the present invention, in accordance with any of the embodiments described herein. The method also comprises providing an aerosol-generating article.

According to a fifth aspect of the present invention there is provided a method of assembling a heater assembly for an aerosol-generating device.

According to a sixth aspect of the present invention there is provided a method of assembling a heater assembly for an aerosol-generating device.

BRIEF DESCRIPTION OF THE DRAWINGS

The invention will now be further described, by way of example only, with reference to the accompanying drawings in which.

DETAILED DESCRIPTION

Advantageously, providing a heater assembly comprising a bushing facilitates the installation of the elongate electrical heater within a housing of an aerosol-generating device. That is, the bushing can be sized and shaped to fit within a housing of an aerosol-generating device.

Advantageously, the aperture through which a portion of the elongate electrical heater extends can facilitate correct positioning of the elongate electrical heater with respect to the bushing. Advantageously, this facilitates correct positioning and orientation of the elongate electrical heater when the heater assembly is installed within a housing of an aerosol-generating device.

Advantageously, the cavity into which a portion of the elongate electrical heater extends facilitates a seal between the elongate electrical heater and the bushing. That is, the cavity can be filled with a sealing material to reduce or eliminate the risk of liquid leakage through the heater assembly between the elongate electrical heater and the bushing.

Preferably, the heater assembly further comprises a potting compound positioned within the cavity. Advantageously, the potting compound provides a seal between the elongate electrical heater and the bushing. Advantageously, the potting compound can maintain the seal at elevated temperatures to which the elongate electrical heater is typically heated during use.

Preferably, the potting compound substantially fills the cavity. Advantageously, substantially filling the cavity with the potting compound may maximise the strength of the seal formed by the potting compound.

Preferably, the potting compound comprises at least one of a thermoset polymer, an epoxy resin, silicone, and combinations thereof. Advantageously, these potting compounds remain stable at elevated temperatures to which the elongate electrical heater is typically heated during use. Advantageously, these potting compounds can be deposited within the cavity in a liquid form and then set, for example by drying or curing. Advantageously, this facilitates ingress of the potting compound into spaces between the elongate electrical heater and the bushing to optimise the seal provided by the potting compound.

Preferably, the potting compound comprises at least one silicone. Advantageously, silicones retain a degree of elasticity after curing, which facilitates a robust seal between the bushing and the elongate electrical heater.

The potting compound may comprise a neutral cure silicone. Neutral cure silicones may exhibit increased elasticity after curing when compared to other silicones, such as acetoxy silicones. Advantageously, an increased elasticity may improve the reliability of the seal provided by the potting compound.

The potting compound may comprise an acetoxy silicone. Acetoxy silicones typically exhibit a reduced curing time when compared to neutral cure silicones. Advantageously, a reduced curing time facilitates manufacture of the heater assembly.

The portion of the elongate electrical heater extending through the aperture may be received within the aperture by an interference fit. That is, the interior cross-sectional dimensions of the aperture may be substantially the same as the exterior cross-sectional dimensions of the portion of the elongate electrical heater extending through the aperture.

Advantageously, an interference fit may secure the elongate electrical heater to the bushing. Advantageously, this may facilitate the use of an elastic potting compound in embodiments in which the heater assembly comprises a potting compound. That is, the interference fit may eliminate the need for the potting compound to secure the elongate electrical heater to the bushing.

Advantageously, an interference fit may prevent relative movement between the elongate electrical heater and the bushing.

Preferably, the bushing comprises a first flange extending around either the first end of the bushing or the second end of the bushing. Advantageously, the first flange may engage a seal between the bushing and a housing of an aerosol-generating device to reduce or prevent liquid leakage between the bushing and the housing of the aerosol-generating device.

Preferably, the first flange extends around the first end of the bushing. Advantageously, this may facilitate engagement between the first flange and a seal when the heater assembly is inserted into a device cavity defined by a housing of an aerosol-generating device. That is, the second end of the heater assembly may be inserted into the device cavity so that a face of the first flange facing away from the first end of the bushing engages a seal.

Preferably, the first flange extends around the first end of the bushing and the bushing further comprises a second flange extending around the second end of the bushing, wherein an annular groove is formed between the first flange and the second flange. Advantageously, the annular groove may receive a gasket to facilitate sealing between the exterior of the bushing and an interior of a housing of an aerosol-generating device.

Preferably, the heater assembly comprises an annular gasket positioned within the annular groove. The annular gasket may be an O-ring. Preferably, the annular gasket is formed from a resilient material. Preferably, the annular gasket is formed from an elastomeric material. The annular gasket may comprise a rubber.

The bushing may be substantially cylindrical. Advantageously, a substantially cylindrical bushing may facilitate insertion of the heater assembly into a device cavity formed by a housing of an aerosol-generating device.

The bushing may comprise a first end face through which the aperture is formed, a second end face in which the cavity is formed, and a substantially cylindrical surface extending between the first end face and the second end face.

In embodiments in which the bushing comprises an annular groove, preferably the annular groove is formed in the substantially cylindrical surface. That is, first and second ends of the substantially cylindrical surface on either side of the annular groove form the first and second flanges respectively.

Preferably, the heater assembly further comprises at least one electrical contact positioned at the second end of the bushing, wherein the at least one electrical contact is electrically connected to the elongate electrical heater. Advantageously, the at least one electrical contact facilitates electrical connection of the elongate electrical heater to at least one of a power supply and control electronics of an aerosol-generating device.

Preferably, the at least one electrical contact comprises at least two electrical contacts.

Preferably, the bushing comprises at least one cut-out positioned on an edge of the bushing. Advantageously, the at least one cut-out may facilitate correct orientation of the heater assembly with respect to a housing of an aerosol-generating device during assembly of an aerosol-generating device comprising the heater assembly. That is, the at least one cut-out may engage at least one projection formed by a housing of an aerosol-generating device.

In embodiments in which the bushing comprises a first flange, the at least one cut-out may be provided on the first flange.

In embodiments in which the bushing comprises a first flange and a second flange, the at least one cut-out may be provided on the first flange, the second flange, or the first flange and the second flange. Preferably, the at least one cut-out comprises at least one cut-out provided on the second flange.

The bushing may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins, vinyl resins, liquid crystal polymers (LCP) and modified LCPs, such as LCPs with graphite or glass fibres.

The bushing may be formed as a single part. The bushing may be formed from at least two parts secured together. The bushing may comprise a first part secured to a second part. The first part may be secured to the second part by at least one of an adhesive, a weld, and an interference fit.

A first portion of the aperture may be formed by the first part of the bushing and a second portion of the aperture may be formed by the second part of the bushing. A first portion of the cavity may be formed by the first part of the bushing and a second portion of the cavity may be formed by the second part of the bushing.

Advantageously, embodiments in which the bushing is formed from a first part secured to a second part may facilitate assembly of the heater assembly. For example, the elongate electrical heater may be positioned between the first part of the bushing and the second part of the bushing when the first part of the bushing is secured to the second part of the bushing. In embodiments in which the portion of the elongate electrical heater extending through the aperture is received within the aperture by an interference fit, this method of assembling the heater assembly may optimise the interference fit without damaging the elongate electrical heater. That is, the two-part assembly of the bushing may reduce or eliminate damage to the elongate electrical heater compared to embodiments in which the elongate electrical heater is inserted through the aperture formed in a single-part bushing.

Preferably, the elongate electrical heater comprises a heating portion extending from the first end of the bushing. Preferably, the heating portion is configured for insertion into an aerosol-generating article. The heating portion may comprise a tapered portion at an end of the heating portion distal from the first end of the bushing. The heating portion may be in the form of a pin. The heating portion may be in the form of a blade. The heating portion may be in the form of a cone.

The elongate electrical heater may be a resistive heater. The elongate electrical heater may comprise an electrically insulating substrate and a resistive heating element provided on the electrically insulating substrate.

Preferably, the electrically insulating substrate is operable at a working temperature of up to about 700 degrees Celsius, more preferably about 800 degrees Celsius. Additionally, or alternatively, the operating temperature of the resistive heating element during use may be about 250 degrees Celsius, more preferably about 300 degrees Celsius.

The electrically insulating substrate may be a ceramic material such as Zirconia or Alumina. Preferably, the electrically insulating substrate has a thermal conductivity of less than or equal to about 2 Watts per metre Kelvin.

The electrically insulating substrate may comprise a planar surface on which the resistive heating element is positioned and a tapered end configured to allow for insertion of the elongate electrical heater into an aerosol-generating article.

Suitable materials for forming the resistive heating element include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® and iron-manganese-aluminium based alloys.

In some embodiments, the resistive heating element comprises one or more stamped portions of electrically resistive material, such as stainless steel. Alternatively, the resistive heating element may comprise a heating wire or filament, for example a Ni—Cr (Nickel-Chromium), platinum, tungsten or alloy wire.

In embodiments in which the heater assembly comprises at least one electrical contact, preferably the resistive heating element is electrically connected to the at least one electrical contact.

According to a second aspect of the present invention there is provided an aerosol-generating device comprising a heater assembly according to the first aspect of the present invention, in accordance with any of the embodiments described herein. The aerosol-generating device and the heater assembly may comprise any of the optional or preferred features described with respect to the first aspect of the present invention.

The aerosol-generating device comprises a housing defining a device cavity for receiving an aerosol-generating article. The heater assembly is positioned within the housing at an upstream end of the device cavity, wherein the elongate electrical heater extends from the first end of the bushing into the device cavity. The aerosol-generating device also comprises a power supply and a controller for controlling a supply of electrical power from the power supply to the elongate electrical heater.

Preferably, the power supply and the control electronics are positioned upstream of the second end of the bushing. That is, preferably, the power supply and the control electronics are separated from the device cavity by the heater assembly.

In embodiments in which the heater assembly comprises a potting compound, advantageously the potting compound reduces or prevents the leakage of liquid from the device cavity through the heater assembly towards the control electronics and the power supply.

Preferably, the aerosol-generating device comprises a gasket positioned between the bushing and the housing. The gasket may form part of the heater assembly. The gasket may be positioned within an annular groove on the bushing, as described herein. Advantageously, the gasket reduces or prevents the leakage of liquid from the device cavity around the outside of the heater assembly towards the control electronics and the power supply.

The power supply may be a DC voltage source. In preferred embodiments, the power supply is a battery. For example, the power supply may be a nickel-metal hydride battery, a nickel cadmium battery, or a lithium based battery, for example a lithium-cobalt, a lithium-iron-phosphate or a lithium-polymer battery. The power supply may alternatively be another form of charge storage device such as a capacitor. The power supply may require recharging and may have a capacity that allows for the storage of enough energy for use of the aerosol-generating device with one or more aerosol-generating articles.

Preferably, the aerosol-generating device comprises at least one air inlet. Preferably, the at least one air inlet is in fluid communication with an upstream end of the device cavity.

The aerosol-generating device may comprise a sensor to detect air flow indicative of a consumer taking a puff. The air flow sensor may be an electro-mechanical device. The air flow sensor may be any of: a mechanical device, an optical device, an opto-mechanical device and a micro electro-mechanical systems (MEMS) based sensor. The aerosol-generating device may comprise a manually operable switch for a consumer to initiate a puff.

The aerosol-generating device may comprise a temperature sensor. The temperature sensor may detect the temperature of the elongate electrical heater or the temperature of an aerosol-generating article received within the device cavity. The temperature sensor may be a thermistor. The temperature sensor may comprise a circuit configured to measure the resistivity of the elongate electrical heater and derive a temperature of the elongate electrical heater by comparing the measured resistivity to a calibrated curve of resistivity against temperature.

Preferably, the aerosol-generating device comprises an indicator for indicating when the elongate electrical heater is activated. The indicator may comprise a light, activated when the elongate electrical heater is activated.

The aerosol-generating device may comprise at least one of an external plug or socket and at least one external electrical contact allowing the aerosol-generating device to be connected to another electrical device. For example, the aerosol-generating device may comprise a USB plug or a USB socket to allow connection of the aerosol-generating device to another USB enabled device. For example, the USB plug or socket may allow connection of the aerosol-generating device to a USB charging device to charge a rechargeable power supply within the aerosol-generating device. The USB plug or socket may additionally, or alternatively, support the transfer of data to or from, or both to and from, the aerosol-generating device. Additionally, or alternatively, the aerosol-generating device may be connected to a computer to transfer data to the device, such as new heating profiles for new aerosol-generating articles.

In those embodiments in which the aerosol-generating device comprises a USB plug or socket, the aerosol-generating device may further comprise a removable cover that covers the USB plug or socket when not in use. In embodiments in which the USB plug or socket is a USB plug, the USB plug may additionally or alternatively be selectively retractable within the device.

According to a third aspect of the present invention there is provided an aerosol-generating system comprising an aerosol-generating device according to the second aspect of the present invention, in accordance with any of the embodiments described herein. The aerosol-generating system also comprises an aerosol-generating article received within the device cavity.

The aerosol-generating article comprises an aerosol-forming substrate.

The aerosol-forming substrate may comprise a plug of tobacco. The tobacco plug may comprise one or more of: powder, granules, pellets, shreds, spaghettis, strips or sheets containing one or more of: tobacco leaf, fragments of tobacco ribs, reconstituted tobacco, homogenised tobacco, extruded tobacco and expanded tobacco. Optionally, the tobacco plug may contain additional tobacco or non-tobacco volatile flavour compounds, to be released upon heating of the tobacco plug. Optionally, the tobacco plug may also contain capsules that, for example, include the additional tobacco or non-tobacco volatile flavour compounds. Such capsules may melt during heating of the tobacco plug. Alternatively, or in addition, such capsules may be crushed prior to, during, or after heating of the tobacco plug.

The aerosol-generating article may have a total length of between approximately 30 millimetres and approximately 100 millimetres. The aerosol-generating article may have an external diameter of between approximately 5 millimetres and approximately 13 millimetres.

The aerosol-generating article may comprise a mouthpiece positioned downstream of the tobacco plug. The mouthpiece may be located at a downstream end of the aerosol-generating article. The mouthpiece may be a cellulose acetate filter plug. Preferably, the mouthpiece is approximately 7 millimetres in length, but can have a length of between approximately 5 millimetres to approximately 10 millimetres.

The tobacco plug may have a length of approximately 10 millimetres.

The diameter of the tobacco plug may be between approximately 5 millimetres and approximately 12 millimetres.

In a preferred embodiment, the aerosol-generating article has a total length of between approximately 40 millimetres and approximately 50 millimetres. Preferably, the aerosol-generating article has a total length of approximately 45 millimetres. Preferably, the aerosol-generating article has an external diameter of approximately 7.2 millimetres.

According to a fourth aspect of the present invention, there is provided a method of generating an aerosol. The method comprises providing an aerosol-generating device according to the second aspect of the present invention, in accordance with any of the embodiments described herein. The method also comprises providing an aerosol-generating article. The aerosol-generating article may comprise any of the optional or preferred features described with respect to the third aspect of the present invention. The method also comprises inserting the aerosol-generating article into the device cavity and heating the aerosol-generating article using the elongate electrical heater.

The step of providing the aerosol-generating article may be performed before or after the step of providing the aerosol-generating device. The steps of providing the aerosol-generating device and providing the aerosol-generating article may be performed together as a single step According to a fifth aspect of the present invention there is provided a method of assembling a heater assembly for an aerosol-generating device. Preferably, the heater assembly is a heater assembly according to the first aspect of the present invention, in accordance with any of the embodiments described herein. The method comprises providing an elongate electrical heater and forming a bushing around a portion of the elongate electrical heater. The bushing defines an aperture at a first end of the bushing and a cavity at a second end of the bushing, wherein the portion of the elongate electrical heater within the bushing extends through the aperture and into the cavity, and wherein the elongate electrical heater extends from the first end of the bushing.

Preferably, the step of forming a bushing comprises inserting a portion of the elongate electrical heater into a mould, injecting a bushing material into the mould and around the portion of the elongate electrical heater positioned within the mould, and setting the bushing material to form the bushing. The setting step may comprise at least one of cooling, drying and curing the bushing material. Preferably, the setting step comprises curing the bushing material. Preferably, the bushing material is a resin.

The bushing may be formed from any of the bushing materials described herein with respect to the first aspect of the present invention.

Preferably, the method further comprises depositing a potting compound within the cavity and setting the potting compound. The step of setting the potting compound may comprise at least one of drying and curing the potting compound. The step of setting the potting compound may comprise exposing the potting compound to at least one of heat, ultra violet radiation, infrared radiation, and moisture, such as at least one of water and water vapour.

Preferably, the step of depositing the potting compound comprises depositing a liquid potting compound into the cavity. The step of depositing the liquid potting compound may comprise at least one of pouring, injecting or flowing the liquid potting compound into the cavity. Preferably, the step of setting the potting compound comprises solidifying the liquid potting compound.

The potting compound may comprise any of the potting compounds described herein with respect to the first aspect of the present invention.

According to a sixth aspect of the present invention there is provided a method of assembling a heater assembly for an aerosol-generating device. Preferably, the heater assembly is a heater assembly according to the first aspect of the present invention, in accordance with any of the embodiments described herein. The method comprises providing a bushing defining an aperture at a first end of the bushing and a cavity at a second end of the bushing. The method also comprises providing an elongate electrical heater and positioning a portion of the elongate electrical heater within the bushing so that the portion of the electrical heater extends through the aperture and into the cavity, and so that the elongate electrical heater extends from the first end of the bushing.

The step of providing the elongate electrical heater may be performed before or after the step of providing the bushing. The steps of providing the bushing and providing the elongate electrical heater may be performed together as a single step.

Preferably, the method further comprises depositing a potting compound within the cavity and setting the potting compound. The step of setting the potting compound may comprise at least one of drying and curing the potting compound. The step of setting the potting compound may comprise exposing the potting compound to at least one of heat, ultra violet radiation, infrared radiation, and moisture, such as at least one of water and water vapour.

Preferably, the step of depositing the potting compound comprises depositing a liquid potting compound into the cavity. The step of depositing the liquid potting compound may comprise at least one of pouring, injecting or flowing the liquid potting compound into the cavity. Preferably, the step of setting the potting compound comprises solidifying the liquid potting compound.

The potting compound may comprise any of the potting compounds described herein with respect to the first aspect of the present invention.

The step of providing the bushing may comprise providing a single-part bushing.

The step of providing the bushing may comprise providing a first part of a bushing and a second part of a bushing. The step of providing the bushing may further comprise securing the first part of a bushing to the second part of a bushing to form the bushing. The step of securing the first part to the second part may comprise at least one of adhering the first part to the second part, welding the first part to the second part, and securing the first part to the second part by an interference fit.

The step of positioning a portion of the elongate electrical heater within the bushing may comprise positioning the portion of the elongate electrical heater between the first part of a bushing and the second part of a bushing before the step of securing the first part of a bushing to the second part of a bushing to form the bushing.

Figure 1:
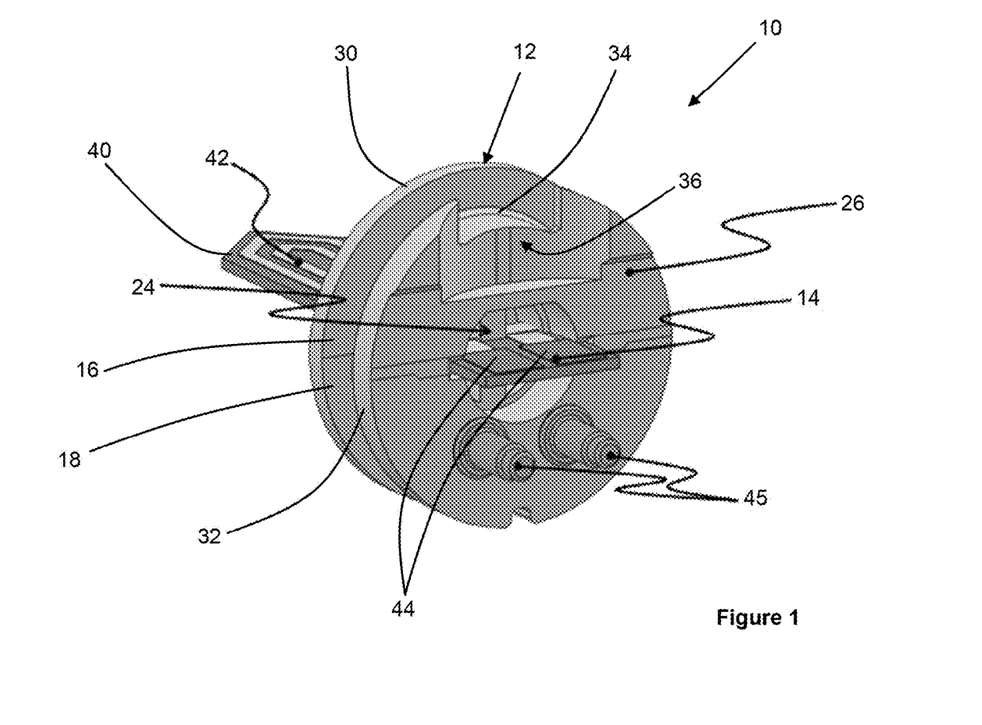
FIG. 1 shows a perspective view of a heater assembly according to an embodiment of the present invention.
Figure 2:
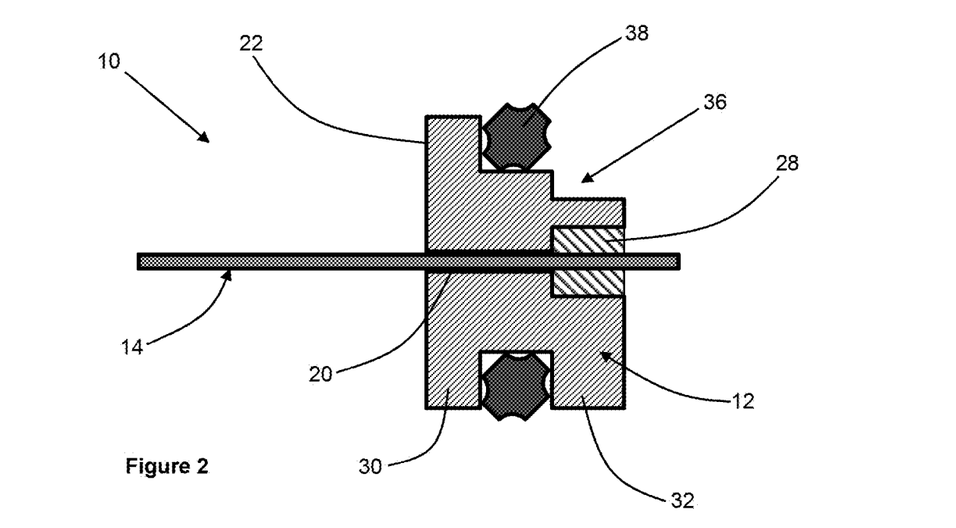
FIG. 2 shows a cross-sectional view of the heater assembly according to FIG. 1 with the addition of a gasket.

FIGS. 1 and 2 show a heater assembly 10 according to an embodiment of the present invention. The heater assembly 10 comprises a bushing 12 and an elongate electrical heater 14.

The bushing 12 comprises a first part 16 and a second part 18 secured together by an interference fit. The bushing 12 defines an aperture 20 at a first end 22 of the bushing 12 and a cavity 24 at a second end 26 of the bushing 12. A portion of the elongate electrical heater 14 extends through the aperture 20 and the cavity 24. The cavity 24 is filled with a potting material 28 to form a seal within the cavity 24 between the bushing 12 and the elongate electrical heater 14. The potting material 28 is omitted from FIG. 1 to show the cavity 24.

The bushing 12 comprises a first flange 30 at the first end 22 of the bushing 12 and a second flange 32 at the second end 26 of the bushing 12. An annular groove 34 is formed between the first and second flanges 30, 32. A cut-out 36 is formed in the second flange 34.

The bushing 12 also comprises a gasket 38 in the form of an O-ring positioned within the annular groove 34. The gasket 38 is omitted from FIG. 1 to shown the annular groove 34.

The elongate electrical heater 14 comprises an electrically insulating substrate 40 and a resistive heating element 42 formed on the electrically insulating substrate 40. The elongate electrical heater 14 also comprises two electrical contacts 44 for providing electrical connection between the resistive heating element 42 and control electronics of an aerosol-generating device comprising the heater assembly 10.

The heater assembly 10 comprises two pins 45 extending from the second end 26 of the bushing 12 to facilitate mechanical connection of the heater assembly 10 within an aerosol-generating device comprising the heater assembly 10.

Figure 3:
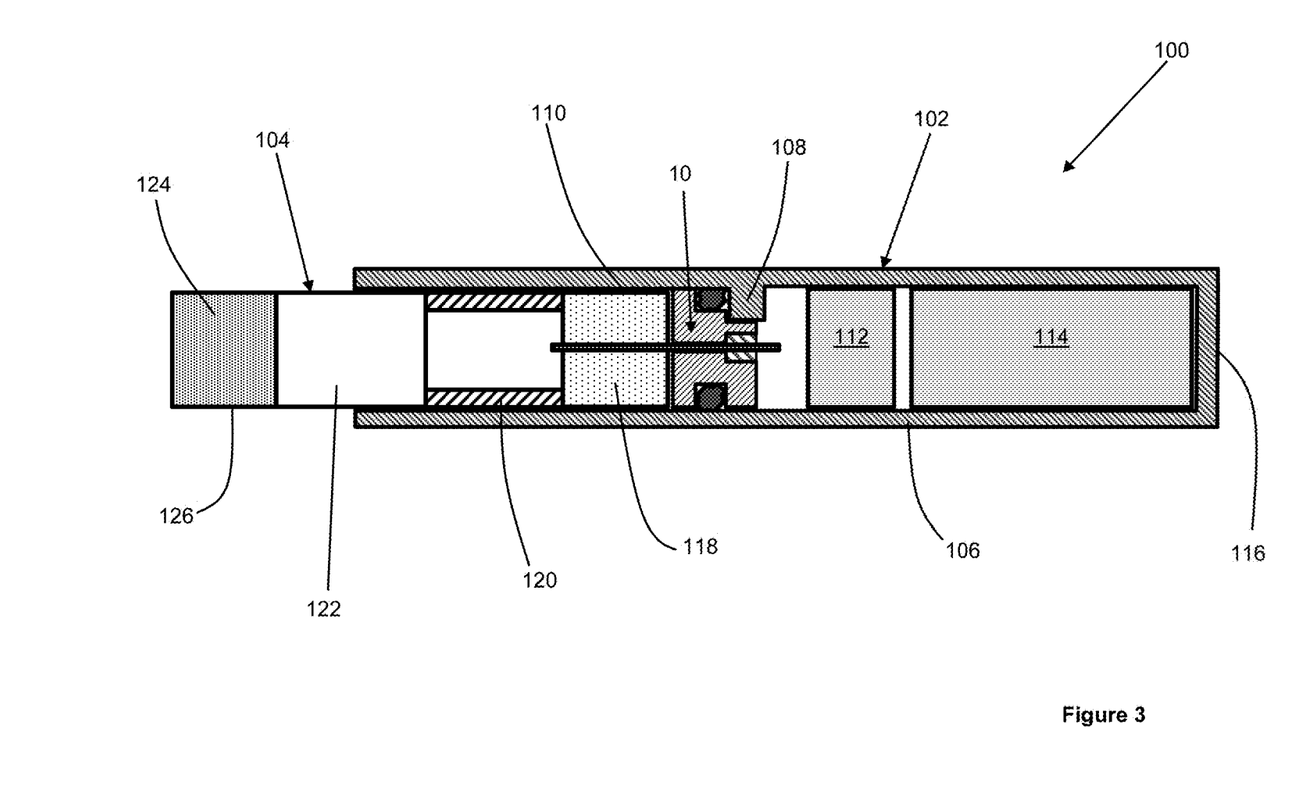
FIG. 3 shows an aerosol-generating system including the heater assembly of FIG. 1.

FIG. 3 shows a cross-sectional view of an aerosol-generating system 100 comprising an aerosol-generating device 102 and an aerosol-generating article 104.

The aerosol-generating device 102 comprises a housing 106 and the heater assembly 10 positioned within the housing 106. The gasket 38 forms a seal between the bushing 12 and an inner surface of the housing 106. The housing 106 comprises a projection 108 that is received within the cut-out 36 of the bushing 12 to ensure correct orientation of the heater assembly 10 within the housing 106.

The housing 106 defines a device cavity 110 for receiving the aerosol-generating article 104, wherein the elongate electrical heater 14 extends from the first end 22 of the bushing 12 into the device cavity 110. A controller 112 and a power supply 114 are positioned within the housing 106 between the heater assembly 10 and a closed end 116 of the housing 106.

The aerosol-generating article 104 comprises an aerosol-forming substrate 118 in the form of a tobacco plug, a hollow acetate tube 120, a polymeric filter 122, a mouthpiece 124 and an outer wrapper 126. When an upstream end of the aerosol-generating article 104 is received within the device cavity 110 of the aerosol-generating device 102, the elongate electrical heater 14 of the heater assembly 10 is received within the aerosol-forming substrate 118.

During use of the aerosol-generating system 100, the controller 112 controls a supply of electrical power from the power supply 114 to the elongate electrical heater 14 to heat the aerosol-forming substrate 118 and form an aerosol for delivery to a user through the mouthpiece 124. The potting material 28 and the gasket 38 substantially prevent the leakage of liquid from the aerosol-forming substrate 118 into the portion of the housing 106 containing the controller 112 and the power supply 114.

Figure 4:
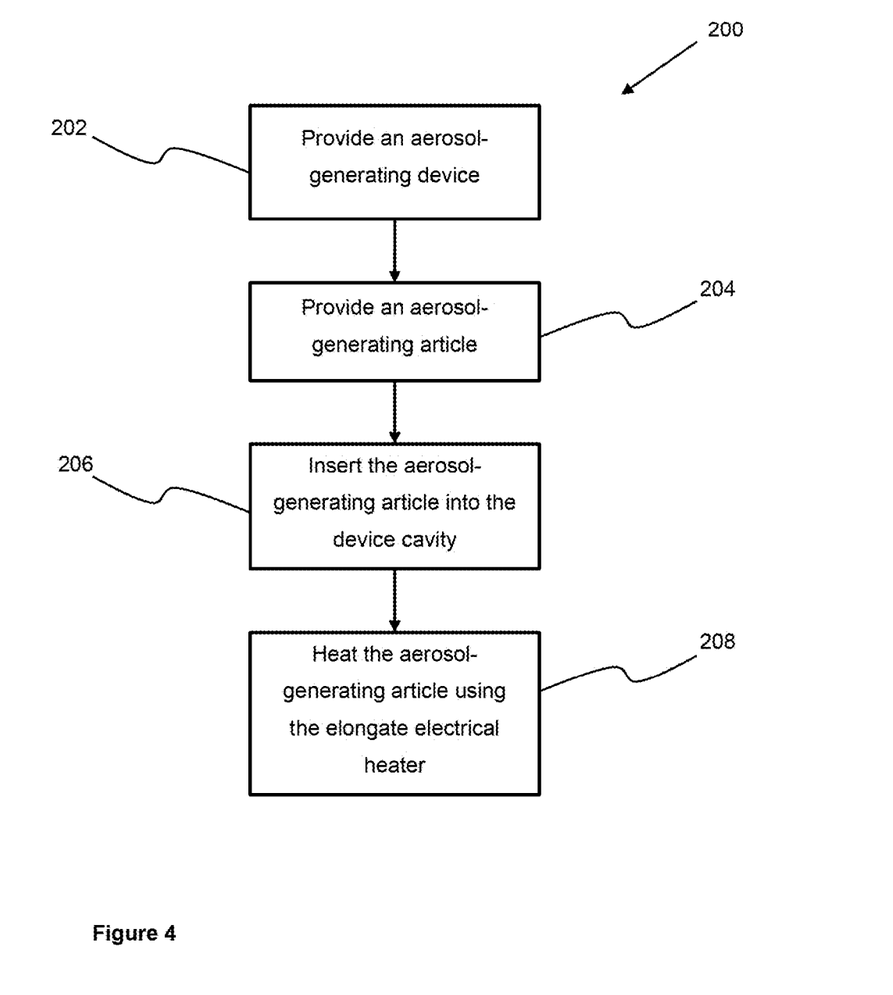
FIG. 4 shows a method of generating an aerosol, according to an embodiment of the present invention.

FIG. 4 shows a method 200 of generating an aerosol, according to an embodiment of the present invention. The method comprises steps 202 and 204 of providing an aerosol-generating device and an aerosol-generating article respectively. The aerosol-generating device comprises a heater assembly according to the present invention. For example, the aerosol-generating device may be the aerosol-generating device 102 shown in FIG. 3. Similarly, the aerosol-generating article may be the aerosol-generating article 104 shown in FIG. 3.

In a step 206 the aerosol-generating article 104 is inserted into the device cavity 110 of the aerosol-generating device 102. In a step 208, the aerosol-generating article 104 is heated using the elongate electrical heater 14 of the heater assembly 10 of the aerosol-generating device 102.

Figure 5:
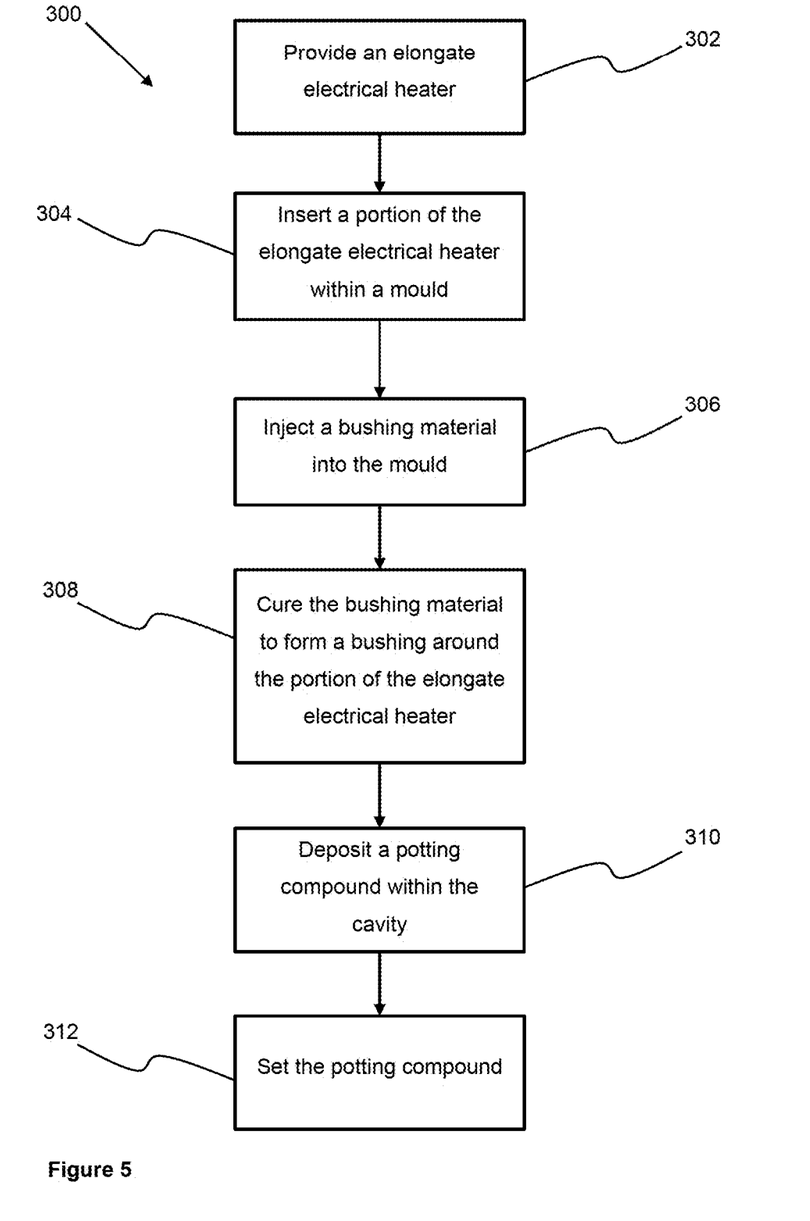
FIG. 5 shows a method of assembling a heater assembly, according to an embodiment of the present invention.

FIG. 5 shows a method 300 of assembling a heater assembly, according to an embodiment of the present invention. The heater assembly may be the heater assembly 10 shown in FIGS. 1 and 2. The method 300 comprises a step 302 of providing an elongate electrical heater 14.

In step 304 a portion of the elongate electrical heater 14 is inserted into a mould. In step 306, a bushing material comprising a resin is injected into the mould and around the portion of the elongate electrical heater 14 positioned within the mould. At step 308, the bushing material is set to form a bushing 12. The setting step comprises curing the resin. The bushing 12 formed in step 308 comprises an aperture 20 and a cavity 24, wherein a portion of the elongate electrical heater 14 extends through the aperture 20 and into the cavity 24 of the bushing 12, and wherein the elongate electrical heater 14 extends from the first end 22 of the bushing 12.

In step 310 a potting compound 28 is deposited within the cavity 24 and in step 312 the potting compound is set. The setting step may comprise at least one of drying and curing the potting compound 28.

The invention claimed is:

1. A heater assembly for an aerosol-generating device, the heater assembly comprising:
a bushing defining an aperture at a first end of the bushing and a cavity at a second end of the bushing, wherein the bushing comprises a first flange extending around either the first end of the bushing or the second end of the bushing; and
an elongate electrical heater extending from the first end of the bushing, wherein a portion of the elongate electrical heater extends through the aperture and into the cavity.

2. The heater assembly according to claim 1, wherein the portion of the elongate electrical heater extending through the aperture is received within the aperture by an interference fit.

3. The heater assembly according to claim 1,
wherein the first flange extends around the first end of the bushing, and
wherein the bushing further comprises a second flange extending around the second end of the bushing and an annular groove formed between the first flange and the second flange.

4. The heater assembly according to claim 3, further comprising an annular gasket positioned within the annular groove.

5. The heater assembly according to claim 1, wherein the bushing comprises a first end face through which the aperture is formed, a second end face in which the cavity is formed, and a cylindrical surface extending between the first end face and the second end face.

6. The heater assembly according to claim 5,
wherein the first flange extends around the first end of the bushing,
wherein the bushing further comprises a second flange extending around the second end of the bushing and an annular groove formed between the first flange and the second flange, and
wherein the annular groove is formed in the cylindrical surface.

7. The heater assembly according to claim 6, further comprising an annular gasket positioned within the annular groove.

8. The heater assembly according to claim 1, further comprising at least one electrical contact positioned at the second end of the bushing, wherein the at least one electrical contact is electrically connected to the elongate electrical heater.

9. The heater assembly according to claim 8, wherein the at least one electrical contact comprises at least two electrical contacts.

10. The heater assembly according to claim 1, wherein the cavity is filled with a potting material to form a seal within the cavity between the bushing and the elongate electrical heater.

11. The heater assembly according to claim 10, wherein the potting material comprises at least one of a thermoset polymer, an epoxy resin, silicone, and combinations thereof.

12. An aerosol-generating device, comprising:
a housing defining a device cavity configured to receive an aerosol-generating article;
the heater assembly according to claim 1, the heater assembly being positioned within the housing at an upstream end of the device cavity, wherein the elongate electrical heater extends from the first end of the bushing into the device cavity;
a power supply; and
a controller configured to control a supply of electrical power from the power supply to the elongate electrical heater.

13. The aerosol-generating device according to claim 12, further comprising a gasket positioned between the bushing and the housing.

14. The aerosol-generating device according to claim 13, wherein the gasket is an annular gasket.

15. The aerosol-generating device according to claim 14,
wherein the bushing comprises a first flange extending around the first end of the bushing and a second flange extending around the second end of the bushing,
wherein the bushing further comprises an annular groove formed between the first flange and the second flange, and
wherein the annular gasket is positioned within the annular groove.

16. An aerosol-generating system, comprising:
the aerosol-generating device according to claim 13; and
the aerosol-generating article received within the device cavity.

* * * * *